United States Patent [19]
Hara

[11] Patent Number: 5,743,900
[45] Date of Patent: *Apr. 28, 1998

[54] HOT TIP CATHETER AND METHOD FOR USING THE SAME

[75] Inventor: Shinji Hara, Tokyo, Japan

[73] Assignee: Sun Star Technology, Inc., Paradise Valley, Ariz.

[*] Notice: The term of this patent shall not extend beyond the expiration date of Pat. No. 5,578,008.

[21] Appl. No.: 467,036

[22] Filed: Jun. 6, 1995

[51] Int. Cl.$^6$ .................................................. A61B 17/36
[52] U.S. Cl. ........................... 606/7; 606/28; 606/31; 607/101; 607/113; 607/134
[58] Field of Search .......................... 606/7, 27–35; 607/100–102, 113, 154–156

[56] References Cited

U.S. PATENT DOCUMENTS

| | | | |
|---|---|---|---|
| 5,078,714 | 1/1992 | Katims | 606/32 |
| 5,087,256 | 2/1992 | Taylor et al. | 606/31 |
| 5,300,068 | 4/1994 | Rosar et al. | 606/32 |
| 5,344,398 | 9/1994 | Hara | |
| 5,364,392 | 11/1994 | Warner et al. | 606/33 |
| 5,370,645 | 12/1994 | Klicek et al. | 606/34 |
| 5,436,566 | 7/1995 | Thompson et al. | 606/32 |
| 5,437,659 | 8/1995 | Leckrone | 606/7 |
| 5,496,312 | 3/1996 | Klicek | 606/34 |
| 5,540,681 | 7/1996 | Strul et al. | 606/31 |
| 5,578,008 | 11/1996 | Hara | 606/27 |

Primary Examiner—Jennifer Bahr
Assistant Examiner—Bryan K. Yarnell
Attorney, Agent, or Firm—Kolisch Hartwell Dickinson McCormack & Heuser

[57] ABSTRACT

A system and method for treating a stenosis or blockage in a bodily fluid passageway is described. The system includes a catheter and a controller for generating radio frequency energy along a pair of output lines, a monitoring circuit for monitoring the phase of the radio frequency energy along the output lines, and an impedance matching circuit for adjusting the output impedance of the generator so that it equals that of a load, e.g., the patient. The catheter includes a catheter body which is insertable into the bodily passageway and operatively connected to the controller. A lumen in the catheter body defines an opening and a stainless steel, metallic-plated mandril is disposed within the lumen so that a terminal end thereof extends through the opening and into the bodily passageway. An internal electrode is joined to the terminal end of the mandril, with the other end of the mandril operatively connected to one of the output lines for receiving the radio frequency energy produced by the generator and delivering such energy to the terminal end and the internal electrode. An external electrode in the form of a grounding pad is located externally of a patient so that when the radio frequency energy is delivered via the mandril to the internal electrode, the same causes or enables the capacitative heating of a stenosis. The method of the present invention relates to finding the most optimal position for placement of the catheter so that optimal power may be delivered to the stenosis.

18 Claims, 3 Drawing Sheets

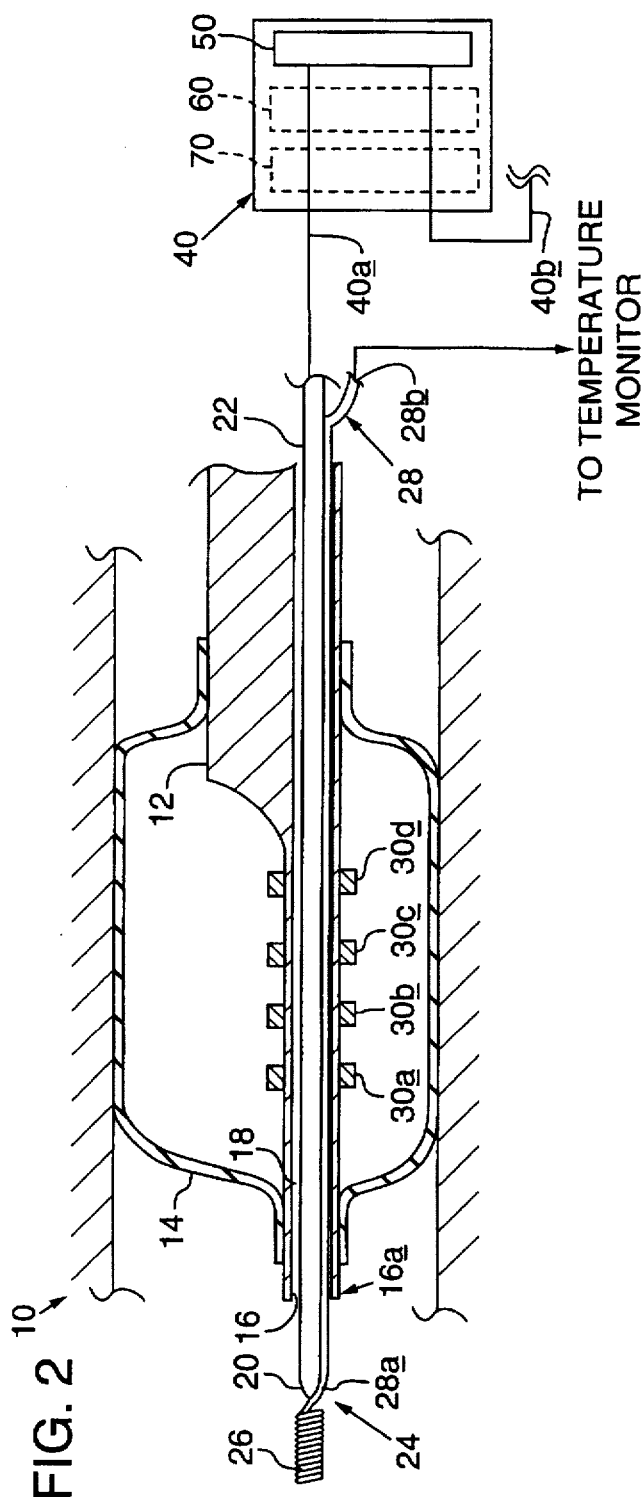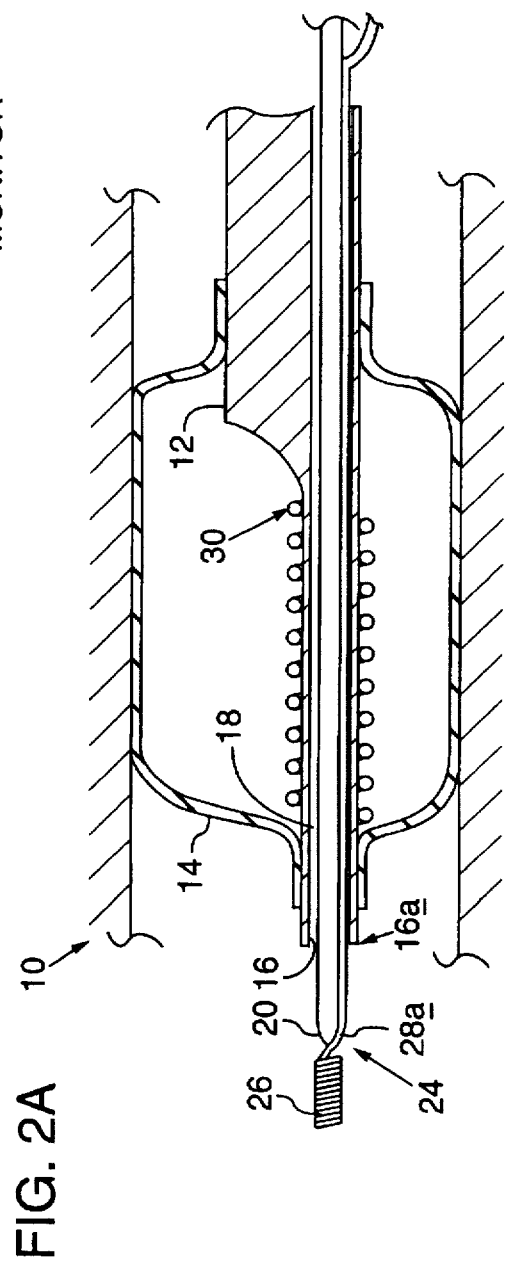

HOT TIP CATHETER AND METHOD FOR USING THE SAME

BACKGROUND

This invention relates generally to the catheterized treatment of a stenosis or blockage in a bodily passageway such as an artery or the like, and more particularly the invention concerns an apparatus and method for determining the optimal placement of the catheter in the bodily passageway for treating the stenosis.

A stenosis is a narrowing or constriction in a bodily passageway such as an artery. One such type of stenosis is known as atherosclerosis and occurs in blood-conveying arteries in humans. Heretofore there have been a variety of apparatuses and methods for treating such stenoses, such as mechanical, ultrasound and laser apparatuses and methods. All of these apparatuses and methods have in mind the ultimate goal of treating a stenosis so that it does not reoccur. The ultimate goal of these treatments is to unblock the stenosis so that it does not return so that a patient who suffers from such condition may go on to lead a normal life.

The apparatuses and methods in the prior art have largely failed to achieve this goal because up until now, discovering the optimal placement of a catheter in a bodily passageway to achieve the most efficient heating of a stenosis has not been available. While the prior art apparatuses and methods have failed to determine the optimal placement of a catheter in an occluded passageway, the present invention has succeeded in providing an improved device and method which reduces the chances of restenosis or a reoccurrence of the stenosis.

With the above problems in mind, it is an object of the present invention to provide an apparatus and method for the treatment of a stenosis which reduces the chances of a reoccurrence.

It is another object of the present invention to provide an apparatus and method for locating the optimal position in a bodily passageway for the treatment of a stenosis.

It is yet another object of the invention to provide a catheter for use in treating a stenosis which uses radio frequency energy to capacitatively heat the same.

It is a further object of the invention to provide a catheter and a controller for delivering radio frequency energy to the catheter, in which the controller includes a system for determining the optimal placement of the catheter in the bodily passageway.

SUMMARY OF THE INVENTION

The invented system and method achieves the above results in the form of a catheter for the treatment of a stenosis in a bodily fluid passageway which includes a controller for generating radio frequency energy along a pair of output lines, monitoring the phase of the radio frequency energy along the output lines, and adjusting the output impedance so that it equals that of a load, e.g., the patient. The catheter includes a catheter body which is insertable into the bodily passageway and operatively connected to the controller. A lumen in the catheter body defines an opening and a mandril is disposed within the lumen so that a terminal end extends through the opening and into the bodily passageway. An internal electrode is joined to the terminal end of the mandril, with the other end of the mandril operatively connected to one of the output lines for receiving the radio frequency energy produced by the generator and delivering such energy to the terminal end and the internal electrode. An external electrode is located externally of the catheter so that when the radio frequency energy is delivered via the mandril to the internal electrode, the same causes or enables the capacitative heating of a stenosis.

The method of the present invention relates to finding the most optimal position for placement of the catheter so that optimal power may be delivered to the stenosis. The method involves the steps of providing a controller, which includes a radio frequency waveform generator, an impedance matching circuit, and a phase monitoring circuit, the controller being operatively connected to the catheter and a grounding pad; inserting the catheter into a bodily passageway so that it is positioned adjacent a stenosis; tuning the impedance matching circuit so that the impedance of the generator matches the output load impedance; delivering a produced waveform to the catheter; and, adjusting the phase of the waveform so that it is substantially 180-degrees out of phase relative to the grounding pad.

These and additional objects and advantages of the present invention will be more readily understood after a consideration of the drawings and the detailed description of the preferred embodiment.

BRIEF DESCRIPTION OF THE DRAWINGS

FIG. 2 is a greatly enlarged view of a catheter according to a second alternate embodiment of the present invention.

FIG. 2A is a greatly enlarged view of the catheter constructed according to the first embodiment of the present invention.

DETAILED DESCRIPTION OF THE PREFERRED EMBODIMENTS

Figure 1:
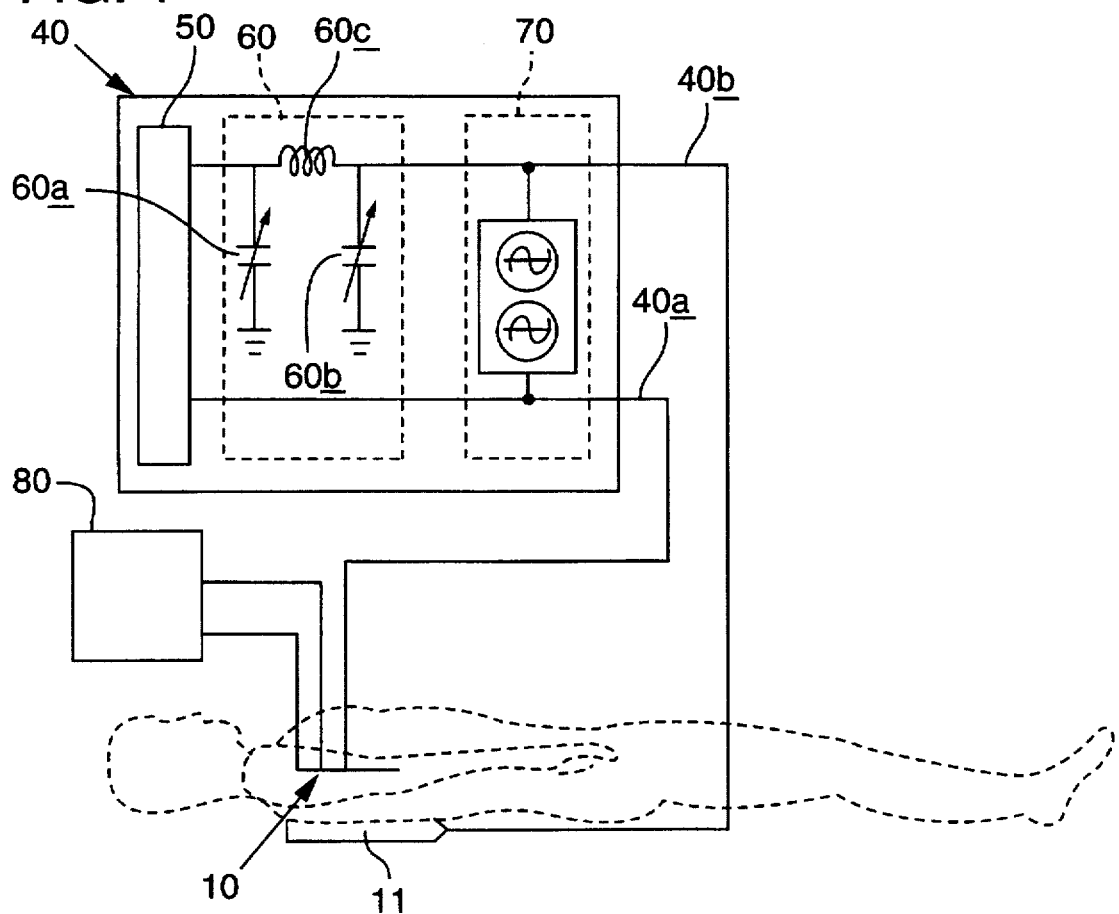
FIG. 1 is a schematic representation of a first embodiment of the present invention being used on a patient undergoing treatment for a stenosis.

The system and method of the present invention according to the preferred embodiment is shown in FIG. 1 where it will be appreciated that a patient is shown undergoing a percutaneous translumenal coronary angioplasty (PTCA) treatment procedure. Although the present invention is described in the context of a PTCA procedure, the invention has utility in a wide variety of medical invasive procedures.

The preferred embodiment of the present invention is described and shown generally in FIG. 1 where a hot tip catheter 10 is operatively connected via output line 40a to a controller 40 which includes a radio frequency wave form generator 50. In the preferred embodiment generator 50 is a crystal-controlled single-frequency generator for supplying a 13.56 MHz signal to the catheter. Controller 40 includes a matching circuit 60 for enabling the output impedance of the generator to be controlled, and a phase monitoring circuit 70 for enabling the controller to monitor the voltage phase between catheter 10 and an external electrode 11 connected to controller 40 via output line 40b.

A temperature monitor 80 is operatively connected to the catheter for monitoring the temperature thereof during the PTCA treatment of a patient and in the preferred embodiment is an integral component of controller 40. More specifically, monitor 80 is interconnected with the matching capacitor in order to search for a matching position which produces a rapid temperature rise of typically 1 degree/sec or larger, either manually, automatically or audibly and described in more detail below.

Catheter 10 is shown in more detail in FIG. 2 where it may be seen that the catheter includes a catheter body 12 having a balloon 14 secured thereto. Preferably balloon 14 has an inflated diameter of around 2 millimeters and a length of around 20 millimeters and is of the type which is suitable for invasive procedures such as will be described. Catheter 10 is shown in a position inside of a bodily passageway which is represented by the cross hatches on either side of balloon 14. A lumen 16 defines a distal end 16a which includes an opening into the bodily passageway. A mandril 18 having a first end 20 and a second end 22 is disposed within lumen 16 in an operative arrangement which allows the heating of a stenosis described in detail below. In the preferred embodiment, mandril 18 is a SUS316L heat-hardened stainless steel rod and may have a length from around between 10 centimeters to 400 centimeters. Typically, however, mandril 18 is around 180 centimeters in length and has a outside diameter of around 0.40 millimeters. Preferably mandril 18 is gold plated for conductivity and includes a teflon coating thereover to facilitate the mandril's manipulability and steerability. First end 20 includes a taper which terminates in a generally pointed region 24. In the preferred embodiment, the taper is around 10 centimeters in length. An internal electrode in the form of a coil spring 26 is preferably constructed of platinum and operatively connected to mandril 18 in region 24 such as by welding. Coil 26 is utilized for capacitatively heating a stenosis described in more detail below. It will be appreciated that for purposes of improved conductivity, pointed region 24 is devoid of the aforementioned teflon coating in the joinder region it shares with electrode 26.

A thermocouple is provided in the form of a constantan wire 28 having an end 28a bonded to pointed region 24 of mandril 18, and another end 28b operatively connected to temperature monitor 80 (FIG. 1). Monitor 80, as mentioned above, is operatively connected to the matching capacitors and utilized to search for a position in which a high temperature rise, typically of 1 degree/second occurs indicating a condition in which the catheter tip is being optimally heated. The thermocouple may be formed by welding constantan wire 28 onto mandril 18. Additionally, a thermocouple sensor comprising a 50-micron copper wire and 50-micron constantan wire may be twisted together to form a 100-micron braid which is operatively coupled to the mandril across its length and anchored to the tip of coil 26 by epoxy adhesive. It will be understood that the epoxy adhesive may be electroconductive.

Energy collection structure in the form of a metal member may be placed near the 13.56 MHz conduction line, which in this case is mandril 18, for effectively collecting the electromagnetic energy by proper phasing of the electromagnetic wave standing in the mandril. Accordingly, the metal member may be heated up without any electrical connection to the mandril. Suitable for practicing an embodiment of the present invention is a single gold member or so-called marker, placed in a conventional PTCA catheter for heating the balloon and surrounding tissues. FIG. 2 shows a preferred embodiment of energy collection structure 30 in the form of a plurality of gold rings 30a through 30d which are spaced along catheter body 12 for collecting radio frequency energy provided by radio frequency generator 50 and through mandril 18 as described above. The rings preferably number more than two and each has a typical length of 1 millimeter. Another preferred embodiment of the present invention is shown in FIG. 2A where it may be seen that collection structure 30 forms a second coil, preferably of gold, having an inner diameter of 0.7 millimeters and suitably engaging lumen 16. The rings and spring may be constructed of any suitable material such as platinum and that any suitable form of energy collection structure may be used.

Figure 3:
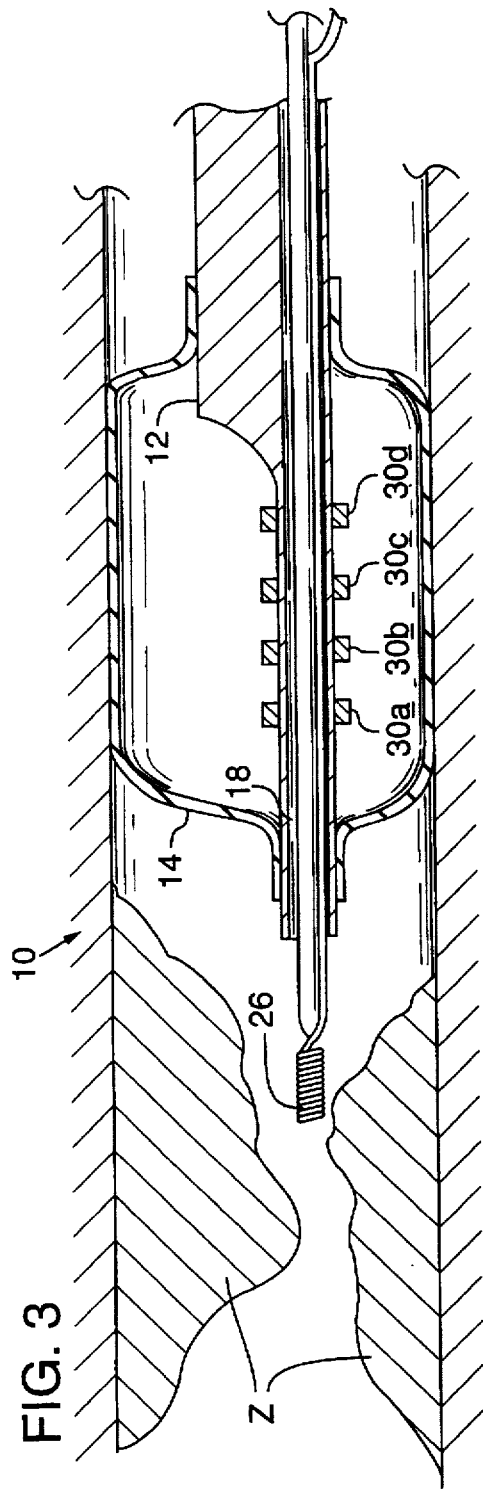
FIG. 3 is a view of the catheter of FIG. 2, in place in a bodily passageway such as an artery, in a position for treating a stenosis.

In operation, catheter body 12 carrying balloon 14 is inserted, as shown in FIG. 3, into a bodily passageway such as an artery having a stenosis or constriction zone Z. Next, the optimal position for heating the stenosis is determined in order to effectively treat the occlusion thereby reducing the possibility of reoccurrence.

In order to determine the optimal heating position in the passageway, the point of minimal reflectance is determined. Because the heating is capacitatively accomplished through the use of a 13.56 MHz signal applied to mandril 18 and coil 26 by controller 40, there must be a smooth flow of power in order to reduce the reflectance of the voltage wave. To minimize the reflectance of the wave and thereby optimally launch the wave into the stenosis or medium for effective treatment, there must be matching field patterns across the boundary between the signal source and stenosis Z. That is, impedance matching of generator 50 is a prerequisite component to place optimal energy across a hypothetical 50-ohm output load.

Digressing for a moment, it will be appreciated that measuring the reflectance of the voltage wave at the tip of the catheter, and more specifically at the tip of coil 26, is a difficult task. By recognizing, however, that the optimal placement, e.g., the true point of minimal reflectance may be evidenced by other indicators utilized in conjunction with generator 50 and matching circuit 60, such indicators may be incorporated for use with catheter 10 for determining the optimal placement thereof. Such other indicators will be described below in conjunction with FIG. 5.

Figure 4:
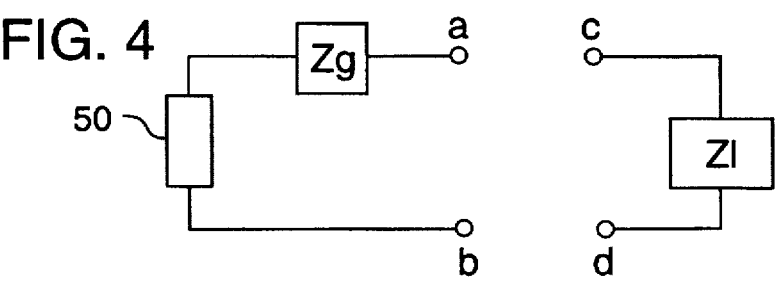
FIGS. 4 and 4A are schematic representations of an impedance matching circuit suitable for use with the first and second embodiments of the present invention.

Shifting attention momentarily, the impedance matching aspect of the preferred embodiment will be discussed. It is generally known that maximum power transfer from a source to an output load takes place when the source impedance and the output load impedance are complex conjugates. In certain instances, as here, when the source and the load do not have complex-conjugate impedances, it is necessary to use an impedance matching device or network to manipulate the impedances so that the source impedance and the load impedance match. Referring now to FIG. 4, generator 50 is schematically represented with an internal impedance of $Z_g = R_g + jX_g$ across two terminals a,b. Generator 50 is to be coupled with an output load, e.g., the patient undergoing treatment, having an impedance between terminals c,d of $Z_L = R_L + jX_L$. In order to maximize the delivery of energy to the stenosis, a condition must exist where $Z_g = Z_L$.

Figure 4A:
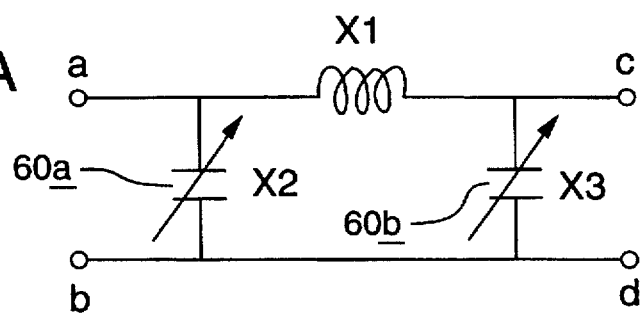

In practice, however, output load $Z_L$ has been found, in the clinical situation, to range from between 100-ohms to 1-kiloohm, and to change further depending upon, among other things, the size of the patient, the placement of the catheter, and the length of the line leading to catheter 10 which may be as long as two meters or more. Matching circuit 60, a portion of which is illustrated in FIG. 4A, is connected between generator 50 and load $Z_L$, and enables the impedance seen by the source, e.g., generator 50, to be adjusted so that it equals $Z'_L=R_g-jX_g$; that is, $R_L$ is transformed to a resistance $R_g$ and $X_L$ to a reactance $-X_g$. More specifically, matching capacitors 60a, 60b (FIGS. 1 and 4A) have reactance values of $X_2$, $X_3$, respectively, and inductor 60c, a value of $X_1$. By solving two simultaneous equations, the design values for $R_{ab}$ and $X_{ab}$, where $R_{ab}=R_g$, and $X_{ab}=-X_g$ may be determined. It will be appreciated that with such values determined and the impedance matched, maximum power may be delivered to the catheter tip in the most optimal manner. It will be understood that the impedance matching step may be performed manually, or automatically such as by a suitably dedicated programmed microprocessor as will be described.

It will further be appreciated that any suitable impedance matching circuit for the waveform frequency generated by generator 50 would do, and that the matching circuit may be reconfigured for other medical procedures which require different frequencies of energy.

Before launching the wave, the optimal position for the catheter must be found. This is accomplished through matching circuit 60 which includes an output voltage detector circuit, an output current detector circuit, and means for determining the output impedance of the generator. It will be understood that if the catheter tip is not touching the stenosis, the impedance across the catheter tip will be different than when the catheter tip is in contact with the stenosis. During RF heating it is important to have firm contact with the tissue or stenosis because if the tip is floating in the blood, matching the impedance of the output circuitry is very difficult because it may be rapidly fluctuating. Thus, in order to efficiently and effectively heat a stenosis, there must be a good, firm contact between the catheter and the stenosis. It should further be understood that the catheter may be initially tuned, manually or automatically as mentioned above, while floating in the artery and then advanced to identify the stenosis (indicated by a change in the impedance seen by the source).

Once the impedance of the output line is properly matched, the catheter is in a position to deliver optimal energy to heat the stenosis. Now, by minutely adjusting matching capacitors 60a, 60b in matching circuit 60, a phase difference of 180-degrees may be developed between the electrode or coil 26 and external electrode 11. By adjusting the matching capacitors as just described, power may be deposited with the highest efficiency at the tip of the catheter to heat the area adjacent coil 26. The adjustment of the capacitors may be accomplished manually by observing the phase over a suitable display, or automatically by a central processing unit programmed to tune the impedance network after positioning of the catheter tip as described above.

Figure 5:
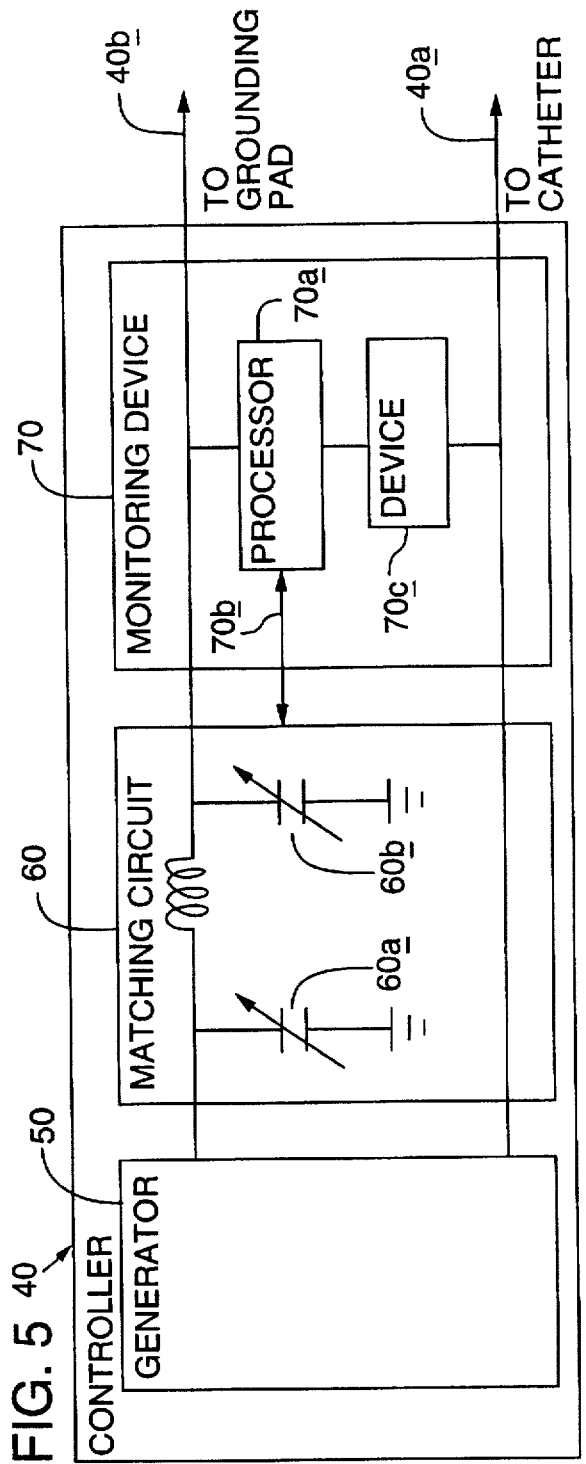
FIG. 5 is a block diagram of the controller constructed according to the preferred and alternate embodiments of the present invention.

In accordance with another preferred embodiment of the present invention, controller 40 may also be seen in FIG. 5. The reader will observe that the controller is substantially the same as the controller described above except for some modifications to monitoring device 70 which will be described in detail below.

As shown, monitoring device 70 is operatively coupled to matching circuit 60 for the purpose of manipulating the matching circuit to maintain a matched impedance between the output impedance of controller 40 and that of a load. A logic processor 70a forms part of monitoring device 70 and is coupled to a device 70c described in more detail below. Processor 70a may be any suitable programmable processor such as a dedicated microprocessor programmed to determine the output impedance in response to input provided from device 70c, and in response thereto adjust matching circuit 60, and more specifically capacitors 60a, 60b so that a substantially matched impedance condition exists between controller 40 and a load.

Device 70c, according to one embodiment, assumes the form of a temperature monitor operatively coupled to thermocouple 28. The temperature monitor, by virtue of its sensitivity to differentially-sensed temperature conditions at internal electrode 26, determines rapid temperature rises, and in response thereto, enables processor 70a via connection 70b, to adjust the matching capacitors so that optimal heating may be achieved.

Device 70c, according to another embodiment, assumes the form of an impedance monitoring circuit for determining the output impedance of the generator and adjusting the matching circuit so that the output impedance of the generator is substantially the same as the impedance of a load.

Device 70c, according to another embodiment, assumes the form of a current flow monitor for monitoring the current flow from the generator and detecting changes related to impedance variations; and further, in response to such changes, adjusting the matching circuit via processor 70a so that the output impedance of the controller is substantially the same as the impedance of a load.

Device 70c, according to yet another embodiment, assumes the form of an ultrasonic signal monitor which is capable of producing an ultrasonic signal and providing such signal to mandril 18, whereupon such signal is reflected from an area internally of the bodily passageway into which the catheter is inserted, and received by the ultrasonic signal monitor. In response to such received signal, the signal monitor enables processor 70a to manipulate matching circuit 60 for maintaining an impedance match between controller 40 and a load.

All of the above embodiments of monitoring device 70, and more specifically device 70c, (except for the phase monitoring circuit described above), provide for the indirect monitoring of the capacitative treatment of the blockage in a bodily passageway. Each of the devices, e.g., the temperature monitor, impedance monitor, current flow monitor, and ultrasonic monitor may best be understood by recognizing that the optimal heating point is close to the minimal reflectance point as measured by the output circuitry, but not exactly at the same point. Other indicators provided by those devices discussed above, e.g., the embodiments of device 70c, provide a way to minutely adjust the impedance matching circuit in response to external variations, so that optimal heating may be achieved at the catheter tip. Such external variations, it will be understood, arise from such things as the variations in the length of the output line from patient to patient, variations in the load impedance experienced during capacitative heating, and so on. It will be further understood that the treatment and techniques described herein are also useful during treatment of a blockage insofar as determining impedance variations during the heating of a stenosis or blockage, and in response thereto, adjusting the matching circuit to accommodate such impedance variations.

It will further be appreciated that the embodiments discussed above are not so limited to applications in the 13.56 MHz range, nor to hot-tip/hot balloon applications. Rather the above-described embodiments will be understood to have a wide range of useful applications in all areas of medical practice in which it is desirable to treat body tissue or blockages in bodily fluid passageways with heat.

A method according to the preferred embodiment of the present invention involves the steps of providing a controller, which includes a radio frequency waveform generator, an impedance matching circuit, and a monitoring device, the controller being operatively connected to the catheter and a grounding pad; inserting the catheter into a bodily passageway so that it is positioned adjacent a stenosis; tuning the impedance matching circuit so that the impedance of the generator matches the output load impedance; delivering a produced waveform to the catheter; and, adjusting the phase of the waveform so that it is substantially 180-degrees out of phase relative to the grounding pad.

Another method according to the preferred embodiment of the present invention involves the steps of providing a controller operatively connected to a catheter and a grounding pad located externally of a bodily fluid passageway, the controller including a radio frequency waveform generator, and impedance matching circuit, and a monitoring device operatively connected to the matching circuit for monitoring the impedance of the controller; inserting the catheter into a bodily fluid passageway so that the catheter tip is positioned adjacent a blockage which represents a component of the output load impedance; determining the output impedance of the controller; and adjusting the matching circuit so that the output impedance of the controller is substantially the same as the impedance of a load.

After heating the stenosis as just described, the stenosis may then be dilated by inflating balloon 14 as conventionally taught in U.S. Pat. No. 5,344,398, the disclosure of which is herein expressly incorporated by reference.

The present invention provides a system and method which achieves many of the objects of the invention and which overcomes many of the drawbacks of the prior art. It should be understood that the invention is not restricted to the particular embodiment which has been described, since variations may be made without departing from the scope of the invention as defined in the claims.

We claim:

1. A catheter for the capacitative-heating treatment of a stenosis in a bodily fluid passageway comprising:
    a controller including a generator for generating radio frequency energy along a pair of output lines, the generator having an output impedance at the output lines the energy at one of the output lines having a phase relative to the other output line, the controller monitoring the phase of the radio frequency energy along the output lines and adjusting the output impedance thereof;
    a catheter body operatively connected to the controller having a lumen defining an opening, and wherein the catheter body is insertable into the bodily passageway;
    a mandril disposed within the lumen having a terminal end which extends through the opening, and another end operatively connected to one of the output lines for receiving the radio opening, and another end operatively connected to one of the output lines for receiving the radio frequency energy and delivering such energy to the terminal end;
    an internal electrode joined to the mandril's terminal end for receiving radio frequency energy; and
    an external electrode outside of the catheter connected to the other output line for permitting the capacitative heating of a stenosis.

2. The catheter of claim 1, wherein the controller includes a dual-channel oscilloscope for monitoring the phase of the radio frequency generator.

3. The catheter of claim 1, wherein the generator is a crystal-controlled, single-frequency generator.

4. The catheter of claim 3, wherein the generator is capable of generating radio frequency energy of 13.56 MHz.

5. The catheter of claim 1, wherein the controller includes a matching circuit for matching the output impedance of the generator with that of a load.

6. The catheter of claim 5 further comprising a microcontroller for automatically manipulating the matching circuit for matching the output impedance of the generator with that of a load.

7. The catheter of claim 1 further comprising a temperature monitor for monitoring the temperature of the catheter.

8. A catheter for the treatment of a stenosis in a bodily fluid passageway comprising:
    a catheter body having a distal end and a balloon secured to the distal end of the body, wherein the body includes a lumen defining an opening adjacent the distal end thereof, and wherein the body is insertable into the bodily passageway so that the lumen provides an opening into the bodily passageway;
    a mandril having a first end and a second end, the mandril being operatively disposed within the lumen so that the first end extends through the lumen opening and into the bodily passageway;
    an internal electrode connected to the mandril adjacent the first end thereof;
    an external electrode outside of the catheter;
    a radio frequency generator operatively coupled to mandril for providing radio frequency energy thereto;
    a thermocouple connected to the internal electrode for sensing the temperature thereof;
    energy collection structure mounted on the catheter body adjacent the lumen for collecting radio frequency energy;
    an impedance matching circuit which includes a pair of matching capacitors operatively coupled between the radio frequency generator and the electrodes for enabling the control of the impedance between the radio frequency generator and the electrodes; and
    a phase monitoring circuit operatively coupled between the radio frequency generator and the electrodes for monitoring the phase of the radio frequency therebetween, and further wherein the internal electrode is a coil capable of capacitatively heating the stenosis.

9. The catheter of claim 8, wherein the coil is constructed of an X-ray opaque metal.

10. A catheter for the treatment of a stenosis in a bodily fluid passageway comprising:
    a catheter body having a distal end and a balloon secured to the distal end of the body, wherein the body includes a lumen defining an opening adjacent the distal end thereof, and wherein the body is insertable into the bodily passageway so that the lumen provides an opening into the bodily passageway
    a mandril having a first end and a second end, the mandril being operatively disposed within the lumen so that the first end extends through the lumen opening and into the bodily passageway:
    an internal electrode connected to the mandril adjacent the first end thereof,
    an external electrode outside of the catheter:
    a radio frequency generator operatively coupled to mandril for providing radio frequency energy thereto;
    a thermocouple connected to the internal electrode for sensing the temperature thereof,
    energy collection structure mounted on the catheter body adjacent the lumen for collecting radio frequency energy;

an impedance matching circuit which includes a pair of matching capacitors operatively coupled between the radio frequency generator and the electrodes for enabling the control of the impedance between the radio frequency generator and the electrodes: and a phase monitoring circuit operatively coupled between the radio frequency generator and the electrodes for monitoring the phase of the radio frequency therebetween, wherein the mandril is constructed from steel and gold plated.

11. A catheter for the treatment of a stenosis in a bodily fluid passageway comprising:

a catheter body having a distal end and a balloon secured to the distal end of the body wherein the body includes a lumen defining an opening adjacent the distal end thereof and wherein the body is insertable into the bodily passageway so that the lumen provides an opening into the bodily passageway a mandril having a first end and a second end, the mandril being operatively disposed within the lumen so that the first end extends through the lumen opening and into the bodily passageway, an internal electrode connected to the mandril adjacent the first end thereof;

an external electrode outside of the catheter;

a radio frequency generator operatively coupled to mandril for providing radio frequency energy thereto;

a thermocouple connected to the internal electrode for sensing the temperature thereof;

energy collection structure mounted on the catheter body adjacent the lumen for collecting radio frequency energy;

an impedance matching circuit which includes a pair of matching capacitors operatively coupled between the radio frequency generator and the electrodes for enabling the control of the impedance between the radio frequency generator and the electrodes;

a phase monitoring circuit operatively coupled between the radio frequency generator and the electrodes for monitoring the phase of the radio frequency therebetween; and a temperature monitor operatively coupled to the matching capacitors for monitoring the temperature change of the internal electrode.

12. A catheter for the capacitative-heating treatment of a blockage in a bodily fluid passageway comprising:

a controller for generating radio frequency energy along a pair of output lines, wherein the controller includes an impedance matching circuit for matching the impedance of the controller with that of a load;

a monitoring device operatively coupled to the matching circuit for monitoring the output impedance of the controller and manipulating the impedance matching circuit so that the output impedance of the controller matches that of a load;

a catheter body operatively connected to the controller and monitoring device, having a lumen defining an opening, and wherein the catheter body is insertable into the bodily passageway;

a mandril disposed within the lumen having a terminal end which extends through the opening, and another end operatively connected to one of the output lines for receiving the radio frequency energy and delivering such energy to the terminal end;

an internal electrode joined to the mandril's terminal end and operatively coupled to the monitoring device for receiving radio frequency energy; and an external electrode outside of the catheter and connected to the other output line for permitting the capacitative heating of a blockage.

13. The catheter of claim 12, wherein the monitoring device includes a logic processor operatively coupled to at least one of the output lines for determining the output impedance of the controller and adjusting the matching circuit so that the output impedance of the controller detects the optimal energy deposition at the stenosis.

14. The catheter of claim 13, wherein the monitoring device includes a thermocouple connected to the internal electrode, and wherein the monitoring device includes a temperature monitor connected to the processor for monitoring the temperature of the internal electrode via the thermocouple and providing input in response thereto, to the processor.

15. The catheter of claim 12 wherein the external electrode and the internal electrode deliver the radio frequency energy in the form of a voltage wave produced therebetween for capacitatively heating the blockage.

16. A method for using capacitative heating to treat a stenosis in a bodily fluid passageway with a catheter which includes an electrode at its tip comprising the steps of:

providing a controller operatively connected to the catheter tip and a grounding pad located externally of the bodily fluid passageway, the controller including a radio frequency waveform generator, and impedance matching circuit, and a monitoring device operatively connected to the matching circuit for monitoring the impedance of the controller;

inserting the catheter into the bodily fluid passageway so that the catheter tip is positioned adjacent a blockage which represents a component of the load impedance;

determining the output impedance of the controller;

applying radio frequency energy in a voltage wave between the catheter tip and the grounding pad for capacitatively heating the stenosis; and adjusting the matching circuit so that the output impedance of the controller is substantially the same as the impedance of a load.

17. The method of claim 16, wherein the adjusting step is performed in part by a programmable logic processor.

18. The method of claim 17, wherein the determining step is accomplished in part by a temperature monitor which monitors the temperature of the catheter tip and provides input to the processor in response thereto.

* * * * *